United States Patent
Hariharan et al.

(10) Patent No.: US 10,293,013 B2
(45) Date of Patent: May 21, 2019

(54) **WATER SOLUBLE *PSIDIUM GUAJAVA* LEAF EXTRACT HAVING STANDARDIZED PHYTOCHEMICALS**

(71) Applicant: PHYTOTECH EXTRACTS PVT LTD, Bangalore (IN)

(72) Inventors: Venkatachalam Hariharan, Bangalore (IN); Pradeepkumar Siddavvanahalli Virupakshappa, Bangalore (IN); Kanchana Hariharan, Bangalore (IN); Paranjothi Kanni, Bangalore (IN); Dipshikha Chakravortty, Bangalore (IN)

(*) Notice: Subject to any disclaimer, the term of this patent is extended or adjusted under 35 U.S.C. 154(b) by 189 days.

(21) Appl. No.: 15/124,736

(22) PCT Filed: Mar. 11, 2015

(86) PCT No.: PCT/IB2015/051759
§ 371 (c)(1),
(2) Date: Sep. 9, 2016

(87) PCT Pub. No.: WO2015/136454
PCT Pub. Date: Sep. 17, 2015

(65) Prior Publication Data
US 2017/0080039 A1    Mar. 23, 2017

(30) Foreign Application Priority Data
Mar. 10, 2014    (IN) .......................... 1213/CHE/2014

(51) Int. Cl.
| | |
|---|---|
| *A23F 3/34* | (2006.01) |
| *A23L 2/52* | (2006.01) |
| *A61K 36/52* | (2006.01) |
| *A61K 36/61* | (2006.01) |
| *A61K 36/62* | (2006.01) |
| *A23L 33/105* | (2016.01) |
| *A61K 36/738* | (2006.01) |

(52) U.S. Cl.
CPC ................ *A61K 36/61* (2013.01); *A23F 3/34* (2013.01); *A23L 2/52* (2013.01); *A23L 33/105* (2016.08); *A61K 36/52* (2013.01); *A61K 36/62* (2013.01); *A61K 36/738* (2013.01); *A23V 2002/00* (2013.01); *A61K 2236/00* (2013.01); *A61K 2236/15* (2013.01); *A61K 2236/17* (2013.01); *A61K 2236/333* (2013.01); *A61K 2236/39* (2013.01)

(58) Field of Classification Search
None
See application file for complete search history.

(56) References Cited

U.S. PATENT DOCUMENTS

2008/0293644 A1* 11/2008 Eidenberger .......... A61K 36/61
514/25

FOREIGN PATENT DOCUMENTS

| JP | 6056923 A | 4/1985 |
|---|---|---|
| WO | 2006090206 A1 | 8/2006 |
| WO | 2009027849 A2 | 3/2009 |

OTHER PUBLICATIONS

Dweck, Anthony C., "A Review of Guava (*Psidium guajava*)", Personal Care Magazine, 6, pp. 33-39, 2005.
Seo, Jongkwon et al., "Study to Find the Best Extraction Solvent for Use with Guava Leaves (*Psidium guajava* L.) for High Antioxidant Efficacy", Food Science & Nutrition, 2(2): pp. 174-180, Feb. 12, 2014.

* cited by examiner

*Primary Examiner* — Michael Barker
(74) *Attorney, Agent, or Firm* — J. Peter Paredes; David G. Rosenbaum; Rosenbaum IP, P.C.

(57) ABSTRACT

The present invention provides a method of obtaining *Psidium guajava* leaf extract standardized to phytochemicals. The extract obtained is highly soluble in water, and contains standardized phytochemicals such as, guijavarin specifically saponins and polyphenols, which may be used in food and beverage products. The method involves the specific method of filtration to obtain highly purified form of phytochemical. The extract obtained is subjected to bioactivity guided fractionation to isolate different compounds to obtain phytochemical enriched fraction followed by purification and isolation of the single phytochemical from the enriched bioactive fraction. The phytochemical is identified as guijaverin, which also exhibits anti-diabetic activity. The *Psidium guajava* leaf extract is useful in food and beverage industries and is used in different formulations such as chocolates, capsules, and aqua based supplement drinks.

8 Claims, 3 Drawing Sheets

WATER SOLUBLE *PSIDIUM GUAJAVA* LEAF EXTRACT HAVING STANDARDIZED PHYTOCHEMICALS

PREAMBLE TO THE DESCRIPTION

The following specification particularly describes the invention and the manner in which it is to be performed:

DESCRIPTION OF THE INVENTION

Technical Field of the Invention

The present invention relates to a method of preparation of guava (*Psidium guajava*) leaf extract containing phytochemicals, more specifically to the method of obtaining *Psidium guajava* leaf extract standardized to phytochemicals, which is useful in food and beverage sector.

Background of the Invention

In recent years, due to poor eating habits, occurrence of lifestyle related diseases such as hypertension, diabetes, brain infarction and heart diseases has increased. The prevalence of these diseases is seen not only in the elder generation but also in the younger generation, posing serious health problems. In many cases, such lifestyle-related diseases are pointed out to be closely related to obesity. Thus, treatment and prevention of obesity through improvement of diet and physical exercise are important for preventing lifestyle-related diseases.

Many dietary compositions are disclosed to overcome obesity. However, these compositions contain chemical compounds, which induce additional health hazards if not monitored properly. Hence, it is preferable to treat these diseases using herbal plants or different plant extracts, which contain natural phytochemicals. The phytochemicals are from natural source and are being increasingly considered for the treatment of various diseases and guava leaf is one of them.

*Psidium guajava*, commonly known as guava, belongs to Myrtaceae family and is grown in tropical regions like Taiwan and Okinawa, India etc. *Psidium guajava* leaf extract contains large amounts of polyphenol substances, tannin substances, saponin, ellagic acid glycosides, flavonoids, etc. A study revealed that the extract exhibits α-amylase inhibitory activity and an effect of inhibiting formation of lipid peroxide. Due to its medicinal properties, *Psidium guajava* leaf supplements are nowadays available in the form of capsules, food supplements and *Psidium guajava* leaf tea. This is highly advantageous, as it avoid side effects resulting from the usage of medicines and drugs.

There are different methods available in the state of art for isolation of *Psidium guajava* leaf extract and also the use of the extract for therapeutic purpose.

The PCT Application No. PCT/IB2005/002172 titled "Improved extracts of *psidium guajava* l., methods for its obtaining and use for the treatment of gastrointestinal disorders" discloses a process of extracting phytomedicaments that contain standardized extracts from the guava plant particularly from its leaves, useful for the treatment of diverse gastrointestinal diseases related to dysfunctions of the nervous system associated to gastrointestinal function. The anti-microbial, anti-motility, anti-spasmolytic, anti-inflammatory, anti-oxidant and anti-secretory properties of the clinically evaluated phytomedicaments of the invention, as well as its null toxicity, allow its usage in the clinic for the treatment of disorders of the gastrointestinal function. The above process fails to use filtration techniques such as spray dried fine powder and chromatographic separation techniques. The above process also does not perform bio assay guided fractionation to study the separated fractions bioactivity for each of the phytocompounds extracted.

The PCT Application No PCT/IB2008/003502 titled "Guava extract" discloses a preparation, isolation and use of an extract of guava fruit. The extract is used for the treatment of a disease or condition related with, caused by or mediated by dipeptidyl peptidase IV. The guava extract contains quercetin related flavonol-glycosides comprising peltatoside and guaijaverin, isoquercetin. The guava extract was effective in inhibiting the activity of dipeptidyl peptidase IV.

Hence, looking at the drawbacks in the state of the art, there is a need for a method of preparing water soluble *Psidium guajava* leaf extract standardized to different phytochemicals such as guijavarin, saponins and polyphenols, which possess beneficial pharmacological properties.

SUMMARY OF THE INVENTION

The invention overcomes the drawbacks in the prior art and provided a method of extraction of leaf extracts from *Psidium guajava* containing standardized phytochemicals such as guijavarin specifically, saponins and polyphenols. The invention discloses a bio activity guided fractionation of the extract to obtain phytochemical enriched fraction, followed by purification and isolation of the single phytochemical from the enriched bioactive fraction. The extract may be incorporated into any food product and beverage product. The extraction method utilizes filtration techniques such as spray drying, which produces spray dried extract that is milled and sieved to get uniform particle size powder. The spray dried powder is analyzed for the presence of polyphenols, saponins and guijavarin content. The extracts containing different phytochemicals are useful for various industries.

The *Psidium guajava* leaf extract thus obtained is very stable in quality and its biological functionality. It has high quantity of bio active polyphenols, flavonoids, anthocyanins and tannins. The *Psidium guajava* leaf extract exhibited high stability after dissolution in aqua base or water. The extract produced showed high solubility and less precipitation and is useful as food and nutrient supplement in different forms such as capsules, chocolates, aqua drinks, tablets etc., also as a raw product or intermediate for producing other beverages and tea infusions containing *Psidium guajava*.

DETAILED DESCRIPTION OF THE INVENTION

In order to more clearly and concisely describe and point out the subject matter of the claimed invention, the following definitions are provided for specific terms, which are used in the following written description.

The term "extract" means a guava extract compositions that are obtained from plant sources, such as leaves, by isolation methods described herein, as the context requires.

The term "Phytochemicals" means chemical compounds that occur naturally in plants such as guijavarin, saponin etc.

Figure 1A:
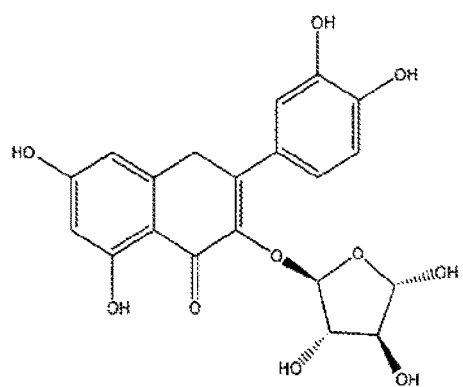
FIG. 1 shows the chemical structure of guijavarin, quercetin and isoquercetin in accordance to one or more embodiments of the invention.
Figure 1B:
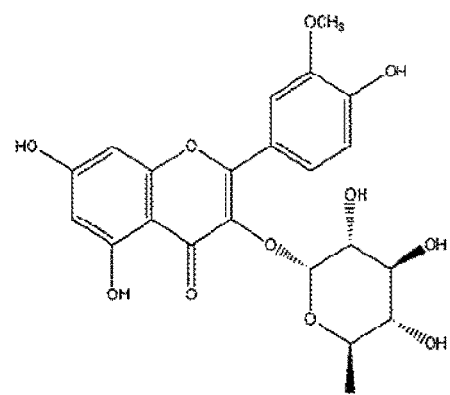
Figure 1C:
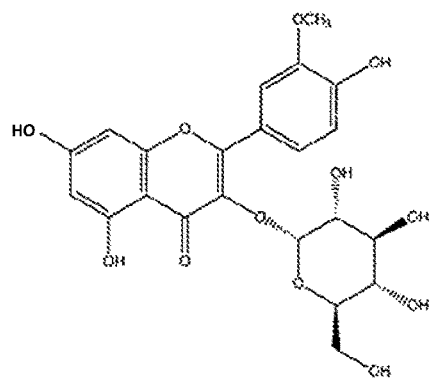

The present invention overcomes the drawback of the prior art by providing a highly improved water soluble *Psidium guajava* leaf extract standardized to specific phytochemicals such as guajavarin, quercetin and isoquercetin. The chemical structure of these phytochemicals is provided in FIGS. 1a, 1b and 1c respectively. The extraction process leads to an extract with high content of phytochemicals.

Quercetin is the aglycone form of number of phytochemicals such as rutin, guaijaverin found in citrus fruit. Quercetin has demonstrated significant anti-inflammatory activity because of direct inhibition of several initial processes of inflammation. For example, it inhibits both the manufacture and release of histamine and other allergic and inflammatory mediators. In addition, it exerts potent antioxidant activity and vitamin C-sparing action.

Figure 2:
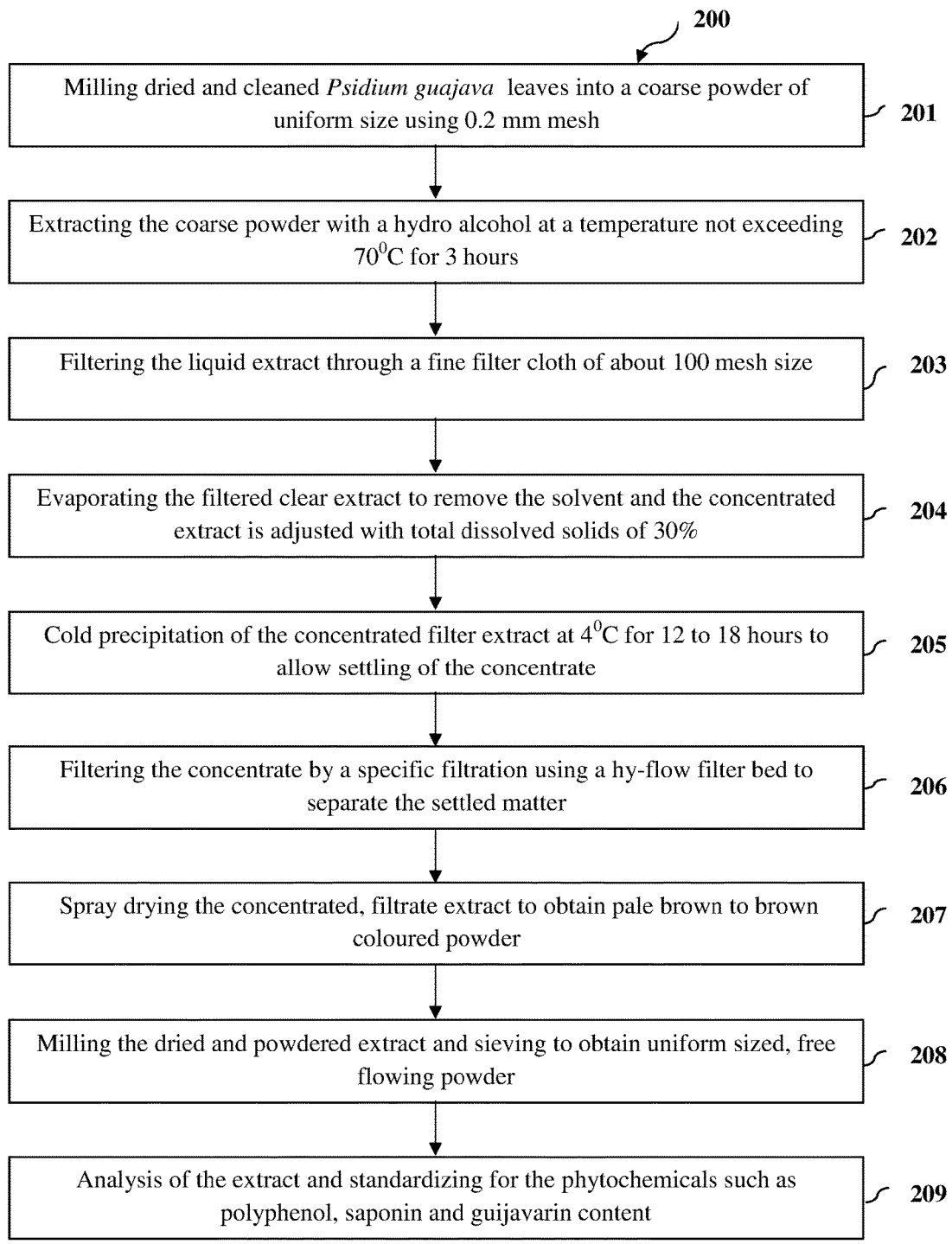
FIG. 2 illustrates the method of extraction of *Psidium guajava* leaf extract.

FIG. 2 illustrates the method of extraction of *Psidium guajava* leaf extract. The method (200) starts with step (201) of milling the dried and cleaned *Psidium guajava* leaves into a coarse powder of uniform size using 0.2 mm mesh. At step (202), the coarse powder is extracted with a hydro alcohol at a temperature not exceeding 70° C. for three hours with continuous circulation of extraction solvent from bottom to top. The hydro alcohol used is a mixture of methanol (70%) and water (30%) and the extraction is carried out in a cone shaped, stainless steel extract. At step (203), the liquid extract is filtered through a fine filter cloth of about 100 mesh size. At step (204), the filtered clear extract is concentrated or evaporated to remove the solvent completely and the concentrated extract is adjusted with total dissolved solids of 30%. At step (205), the concentrated filter extract is subjected to cold precipitation at 4° C. for a period of 12 to 18 hours to allow settling of the concentrate. At step (206), the concentrate is filtered by a specific filtration using a by-flow filter bed to separate the settled matter. At step (207), the concentrated, filtrate extract is subjected to spray drying. The temperature of the drier is validated and set in such a way to obtain pale brown to brown coloured powder. At step (208), the dried and powdered extract is milled and sieved to obtain uniform sized, free flowing powder. At step (209), the extract is analysed and standardized for the phytochemicals such as polyphenol, saponin and guijavarin content.

The extraction method results in highly potent *Psidium guajava* extract. The method employed is also a sophisticated method for producing the excellent product suitable for food and beverage uses. The method also involves specific purification techniques to obtain highly purified extract.

Figure 3:
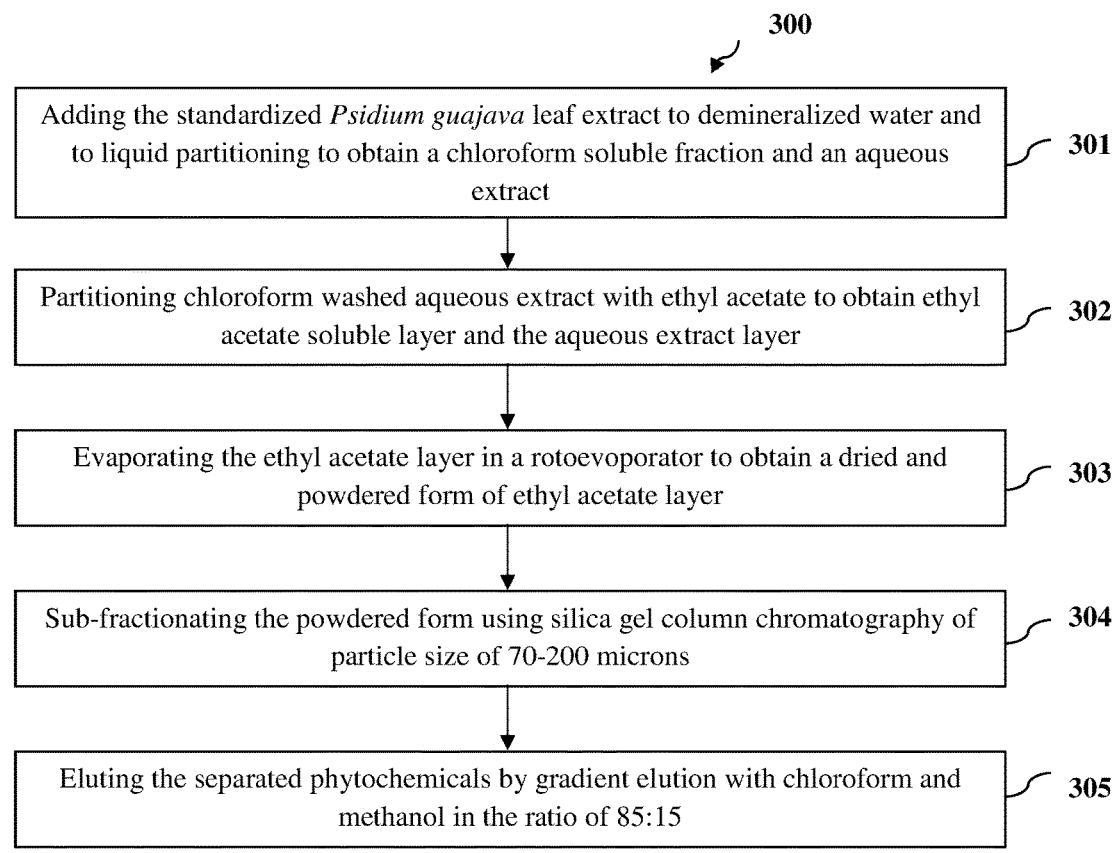
FIG. 3 illustrates method of isolation of phytochemicals from the *Psidium guajava* leaf extract.

FIG. 3 illustrates the isolation of phytochemicals from the *Psidium guajava* leaf extract. The *Psidium guajava* leaf extract, thus obtained, is used to isolate the phytochemicals. The method (300) of isolation of phytochemicals from the *Psidium guajava* leaf extract starts at the step (301) by adding the standardized *Psidium guajava* leaf extract to demineralized water and further to liquid partitioning using chloroform to obtain a chloroform soluble fraction and an aqueous extract. At step (302), the chloroform washed aqueous extract is further partitioned with ethyl acetate to obtain ethyl acetate soluble layer and the aqueous extract layer. At step (303), the ethyl acetate layer is concentrated in a rotoevoporator to obtain a dried and powdered form of ethyl acetate layer. At step (304), the powdered form is sub-fractionated using silica gel column chromatography of particle size of 70-200 microns. At step (305), the separated phytochemicals are eluted by gradient elution with chloroform and methanol in the ratio of 85:15.

The ethyl acetate layer is subjected to silica gel column chromatography using gradient elution with different ratio of chloroform and methyl alcohol ranging from 100:1 to 85:15 for each fraction. Silica gel column chromatography results in separation of six fractions namely PGF-1 (*Psidium Guajava* Fraction-1) separated using 94% chloroform and 6% methanol, PGF-2 separated using 93% chloroform and 7% methanol, PGF-3 separated using 91% chloroform and 9% methanol, PGF-4 separated using 88-82% chloroform and 12-18% methanol, PGF-5 separated using 79-0% chloroform and 21-100% methanol and PGF-6 is ethyl acetate partitioned layer.

The separated fractions are subjected to qualitative analysis using thin-layer chromatography (TLC) and high performance liquid chromatography (HPLC). TLC is carried out using silica gel as stationery phase and toluene, ethyl acetate and acetic acid in the ratio of 45:45:10 as mobile phase. The separated fractions are also subjected to HPLC. Further, the phytochemicals are subjected to quantitative analysis for determination of molecular weight by liquid chromatography-electrospray ionization-mass spectroscopy. Finally, the phytochemicals are chemically characterized by Nuclear Magnetic Resonance (NMR), Ultra-violet (UV) and Infrared Spectroscopy (IR) analysis. The purity of the phytochemical obtained is 99%.

The chemical characterization of the phytochemicals resulted in the presence of kaempherol-3-O-glycoside, quercetin-3-O-$\alpha$-L-arabinopyranoside (guijaverin).

The guijaverin obtained by the above process is screened for the bioactivity i.e. for the anti-diabetic activity (Alpha-glucosidase inhibition, Alpha-amylase inhibition and lipase inhibition). The pre-incubation mixture contained 80 mM phosphate buffer pH 7.0, vehicle buffer, positive control, test sample of various concentrations and 50 µl of Alpha-glucosidase. The reaction mixture is mixed and pre incubated at 37° C. for 30 minutes. The sucrose as substrate is added to a final concentration of 23.125 mM and the reaction mixture is mixed and incubated at 37° C. for 50 minutes. The reaction is arrested by keeping in boiling water bath for 2 minutes and then cooled to room temperature. 250 µl of glucose reagent is added to 50 µl of reaction mixture and mixed and incubated at 25° C. for 10 minutes. The absorbance is measured at 510 nm in a micro-plate reader. A control reaction is carried out without the test sample.

The extract exhibited dose-dependent inhibition of the alpha-glucosidase thus indicating the anti-diabetic activity of the extract.

The *Psidium guajava* leaf extract is useful in major industries of food and beverage sector in different forms such as chocolates, capsules, and aqua based supplement drinks etc. The extract is also useful in the Pharmaceuticals, cosmetics, neutraceuticals etc.

The *Psidium guajava* leaf extract is useful in production of food and beverage products containing guava extract produced from above invention such as a choco compound containing *Psidium guajava* extract and other herbal extracts containing polyphenols and flavonoids. The choco compound is useful in reducing headache, body ache, nausea, burning sensation and also exhibits hepatoprotective activity.

The *Psidium guajava* leaf extract is also produced as a capsule in combination with other herbal extracts such as *Rosa roxburgii* (Sweet chestnut rose), *Engelherdtia chinan-* sis (Kohki) and *Nelumbe nucifera*. The capsule exhibits hepatoprotective activity, cough suppressive activity and anti-diabetic activity.

In addition to the above mentioned formulations, the *Psidium guajava* leaf extract is also used as a natural tea. The natural tea contains guava extract in combination with mulberry leaves and *Camellia sinensis* leaves. The *Psidium guajava* tea helps in prevention of diabetes and also reduces the blood sugar level in diabetics, exhibits hepatoprotective activity. It also acts as a natural appetizer and refresher.

The aqua based herbal drinks of *Psidium guajava* leaf extract such as herbal decoctions acts as an antioxidant and cardioprotective agent.

We claim:

1. A method for preparation of water soluble *Psidium guajava* leaf extract, the method comprising the steps of:
   a. milling the dried and cleaned *Psidium guajava* leaves into a coarse powder of uniform size using 0.2 mm mesh (201);
   b. extracting the coarse powder with a hydro alcohol at a temperature not exceeding 70° C. for a period of 3 hours (202);
   c. filtering the liquid extract through a fine filter cloth of about 100 mesh size (203);
   d. evaporating the filtered clear extract to remove the hydro alcohol completely and adjusting the concentrated extract with one or more total dissolved solids of 30% (204);
   e. allowing the concentrated filter extract to settle as a concentrate by subjecting to cold precipitation at 4° C. for 12 to 18 hours (205);
   f. filtering the concentrate using a by-flow filter bed to separate the settled matter (206);
   g. spray drying the filtrate extract to obtain pale brown to brown coloured powder (207);
   h. milling the dried and powdered extract and sieving to obtain uniform sized, free flowing powder (208); and
   i. analyzing the extract for the presence of phytochemicals (209).

2. The method as claimed in claim 1, wherein the hydro alcohol used is a mixture of methanol and water in the ratio of 70:30.

3. The method as claimed in claim 1, wherein phytochemicals analyzed include polyphenol, saponin and guijavarin.

4. The method as claimed in claim 1, wherein the obtained *Psidium guajava* leaf extract in combination with one or more herbal extracts comprising of *Rosa roxburgii* (Sweet chestnut rose), *Engelherdtia chinansis* (Kohki) and *Nelumbe nucifera* exhibits hepatoprotective activity, cough suppressive activity and anti-diabetic activity.

5. The method as claimed in claim 1, wherein the obtained *Psidium guajava* leaf extract in combination with *Camellia sinensis* exhibits anti-diabetic activity, a natural appetizing property and refreshing property.

6. The method as claimed in claim 1, wherein the obtained *Psidium guajava* leaf extract exhibits antioxidant and cardioprotective property.

7. A method of isolation of phytochemical from a *Psidium guajava* leaf extract, the method comprising the steps of:
   a. subjecting the leaf extract in demineralized water and to liquid partitioning using chloroform to obtain a chloroform soluble fraction and an aqueous extract (301);
   b. liquid partitioning the chloroform washed aqueous extract with ethyl acetate to obtain an ethyl acetate soluble layer and an aqueous extract layer (302);
   c. evaporating the ethyl acetate layer in a rotoevoporator to obtain a dried and powdered form of ethyl acetate layer (303);
   d. sub-fractionating the powdered form of ethyl acetate layer using silica gel column chromatography of particle size of 70-200 microns (304); and
   e. eluting the separated phytochemicals by gradient elution with chloroform and methanol in the ratio of 85:15 (305).

8. The method as claimed in claim 7, wherein elution of the phytochemicals is achieved using silica gel column chromatography with chloroform and methyl alcohol resulting in one or more fractions comprising kaempherol-3-O-glycoside and guijaverin.

* * * * *